United States Patent
Kim et al.

(10) Patent No.: US 7,487,051 B2
(45) Date of Patent: Feb. 3, 2009

(54) EVALUATING METHOD OF THE FRACTURE TOUGHNESS USING THE CONTINUOUS INDENTATION METHOD

(75) Inventors: Kwang-Ho Kim, Seoul (KR); Jung-Suk Lee, Gyeonggi-do (KR); Yang-Won Seo, Seoul (KR); Yeol Choi, Seoul (KR)

(73) Assignee: Frontics, Inc. (KR)

( * ) Notice: Subject to any disclaimer, the term of this patent is extended or adjusted under 35 U.S.C. 154(b) by 0 days.

(21) Appl. No.: 11/667,229

(22) PCT Filed: Sep. 14, 2005

(86) PCT No.: PCT/KR2005/003039

§ 371 (c)(1),
(2), (4) Date: May 8, 2007

(87) PCT Pub. No.: WO2006/052060

PCT Pub. Date: May 18, 2006

(65) Prior Publication Data

US 2008/0010031 A1    Jan. 10, 2008

(30) Foreign Application Priority Data

Nov. 9, 2004  (KR)  ............... 10-2004-0091013

(51) Int. Cl.
*G01L 1/00* (2006.01)
(52) U.S. Cl. ............... 702/42; 73/81; 73/82; 73/865.3; 702/33
(58) Field of Classification Search ............ 702/33–35, 702/42, 44, 156; 73/81, 82, 856, 865.3; 324/209, 324/223
See application file for complete search history.

(56) References Cited

U.S. PATENT DOCUMENTS

| | | | |
|---|---|---|---|
| 4,852,397 A | 8/1989 | Haggag | |
| 5,602,329 A | 2/1997 | Haubensak | |
| 6,053,034 A | 4/2000 | Tsui et al. | |
| 6,134,954 A * | 10/2000 | Suresh et al. | 73/81 |
| 6,247,355 B1 * | 6/2001 | Suresh et al. | 73/82 |
| 2003/0183021 A1 * | 10/2003 | Holmberg | 73/865.3 |

OTHER PUBLICATIONS

International Search Report for PCT/KR2005/003039 dated Dec. 20, 2005 ISA/KR.

* cited by examiner

*Primary Examiner*—John H Le
(74) *Attorney, Agent, or Firm*—Harness, Dickey & Pierce, P.L.C.

(57) ABSTRACT

The present invention relates to a method of evaluating the fracture toughness of a material using the continuous indentation technique. In the method of this invention, the stress coefficient, strain hardening modulus and yield stress of the material are determined using the continuous indentation technique and, thereafter, the reduced elastic modulus (Er) of the material is calculated. The effective elastic modulus and the initial elastic modulus are calculated and, thereafter, the damage parameter is calculated using the void volume fraction. The critical elastic modulus and the characteristic fracture initiation point of the indentation depth are determined using the damage parameter and, thereafter, the fracture toughness of the material is evaluated. The present invention is advantageous in that the fracture toughness of a brittle material can be evaluated precisely using a nondestructive evaluation technique.

10 Claims, 4 Drawing Sheets

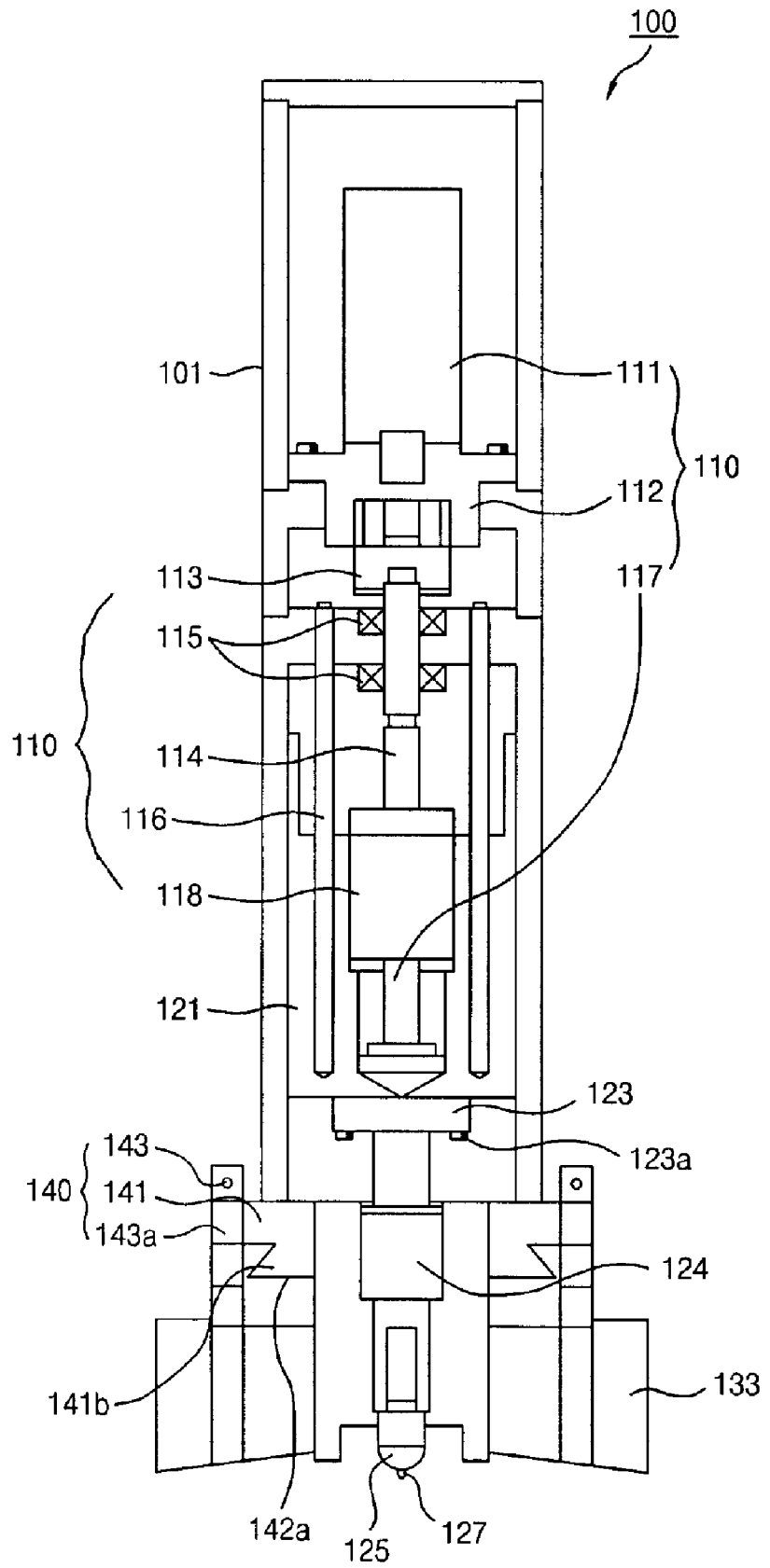
[Fig. 1]

[Fig. 2]
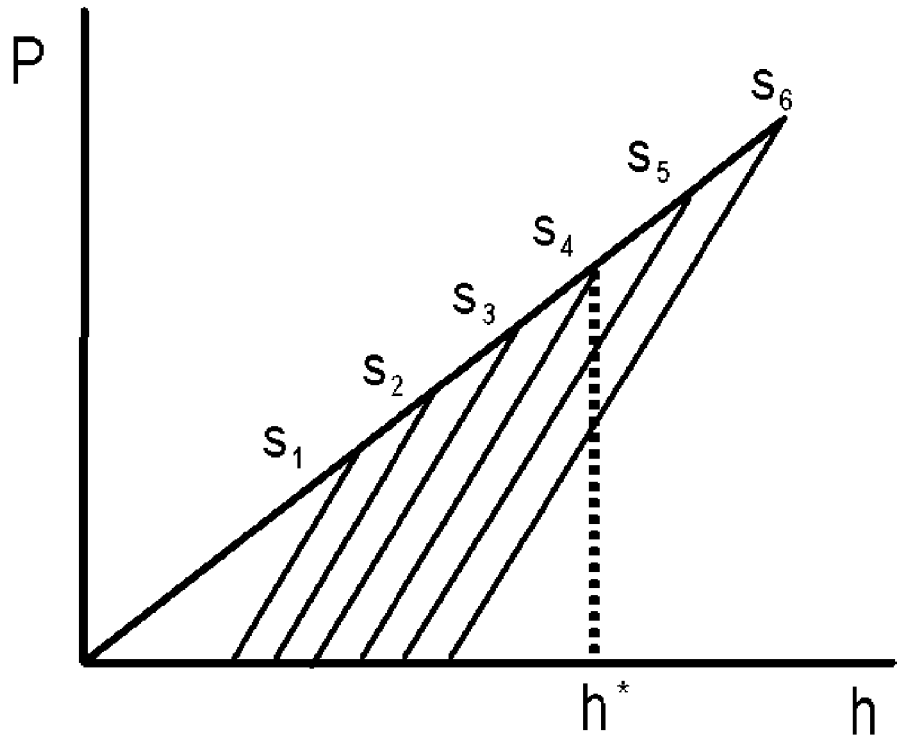
$S_{1\sim 6}$ : Unloading curve slope
[Fig. 3]
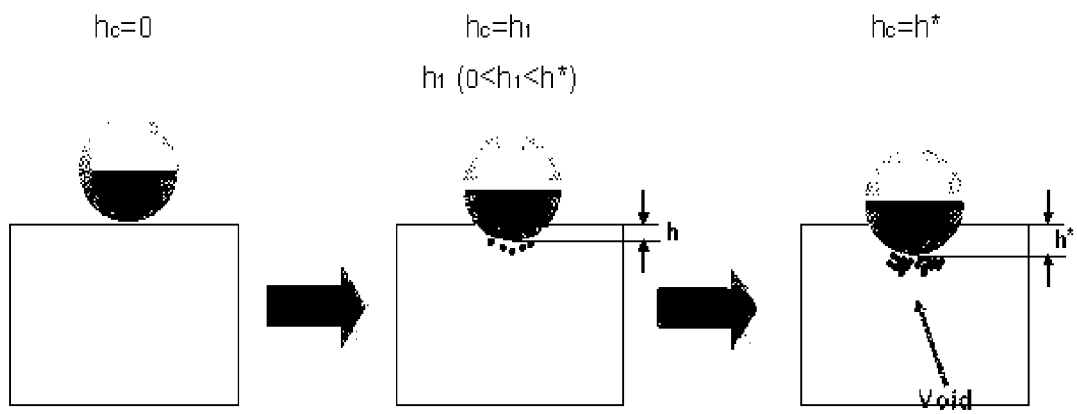
[Fig. 4]
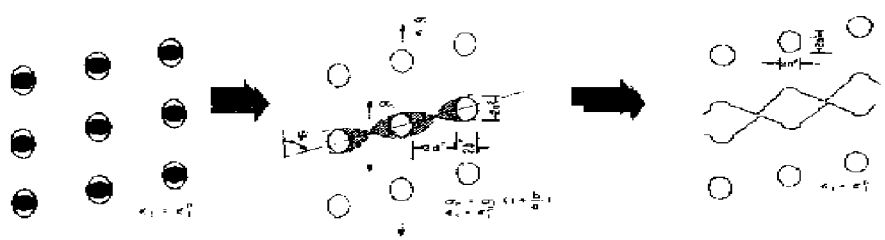

[Fig. 5]
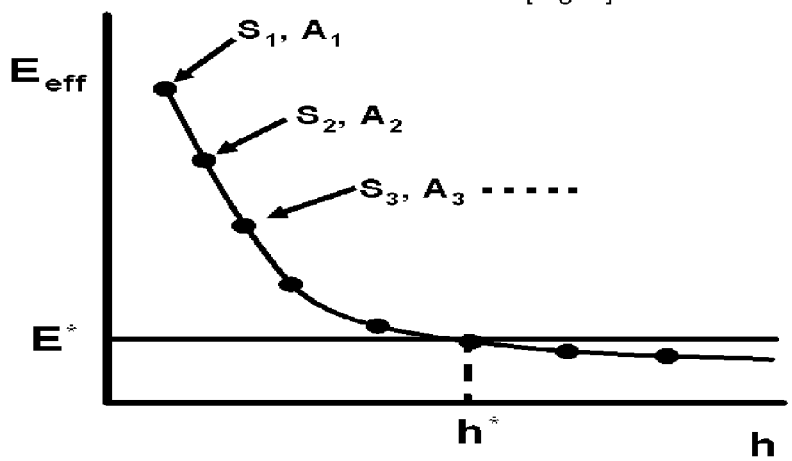
[Fig. 6]
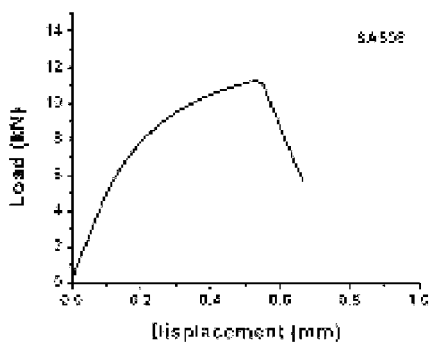
[Fig. 7]
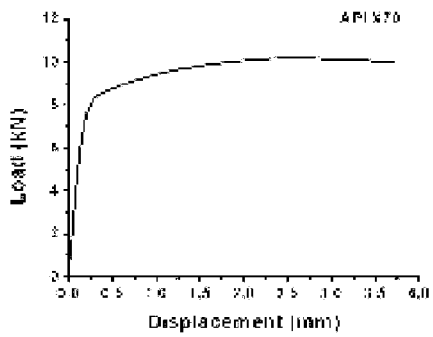
[Fig. 8]
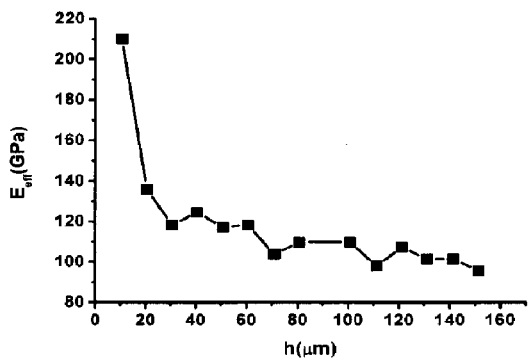

[Fig. 9]
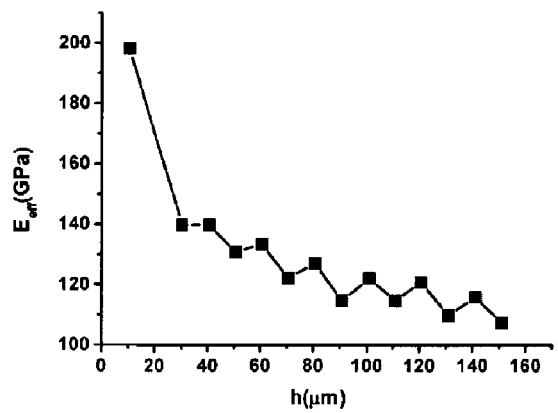
[Fig. 10]
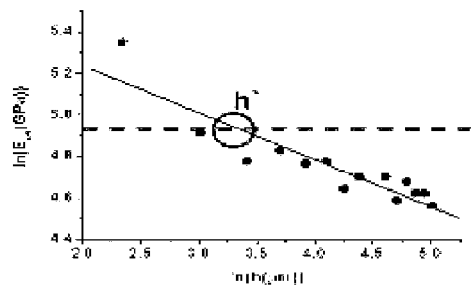
[Fig. 11]
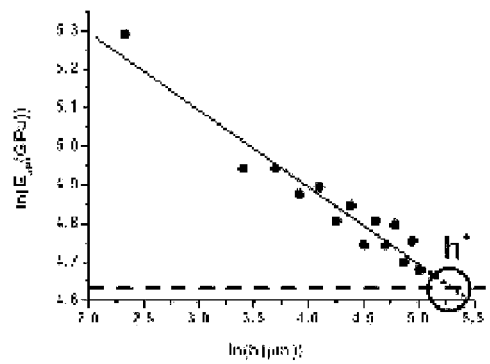
[Fig. 12]
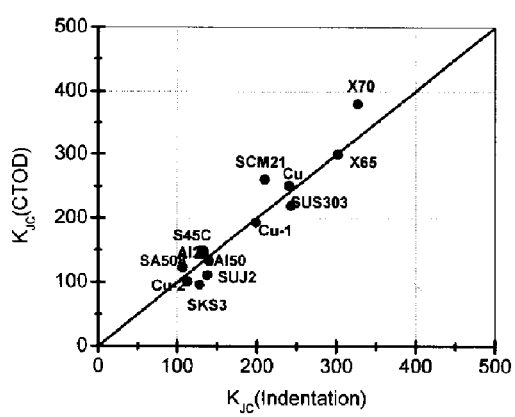

EVALUATING METHOD OF THE FRACTURE TOUGHNESS USING THE CONTINUOUS INDENTATION METHOD

TECHNICAL FIELD

The present invention relates, in general, to methods for evaluating fracture toughness of materials using a continuous indentation technique and, more particularly, to a method for evaluating the fracture toughness of a material using the continuous indentation technique, wherein the elastic modulus of the material corresponding to an indentation depth is primarily determined using the continuous indentation technique and, thereafter, the characteristic fracture initiation point of the indentation depth is determined, so that the fracture toughness of a brittle material can be determined precisely using a nondestructive evaluation technique based on the relationship between energy, continuously absorbed by the material until the indentation depth has reached the characteristic fracture initiation point, and the fracture energy of the material.

BACKGROUND ART

Fracture Toughness ($K_{JC}$), which represents the crack growth resistance of a material, is an important property of the material when evaluating the structural soundness of the material. However, conventional fracture toughness evaluation methods must require test-pieces having specified shapes and sizes in order to be reliable. In other words, a crack is preformed in a test-piece and, thereafter, stress and strain around the crack are mechanically analyzed, so that an appropriate test capable of determining the crack size and the crack growth direction can be conducted. Thereafter, fracture conditions can be determined using the test. Examples of representative fracture toughness tests are a compact tension test and a three-point-single edge notched bend test, each of which uses fatigue precracking. To execute the above-mentioned tests, a plurality of test-pieces having specified crack growth directions and crack sizes (refer to ASTM standards about the loading direction and crack growth direction) must be produced from a material. The crack growth of the material can be determined while fracturing the test-pieces.

However, the complex test procedure, which includes the fatigue precracking and the crack length evaluation, makes it difficult to evaluate the fracture toughness. Furthermore, the conventional fracture toughness evaluation method uses a destructive technique in which a test-piece is cut from a material. Thus, the conventional method cannot be adapted to actively operated industrial structures.

To mitigate the above-mentioned problems experienced in the conventional fracture toughness evaluation method, a variety of fracture toughness evaluation theories and models using indentation techniques have been studied and developed. However, the conventional theories and models to evaluate the fracture toughness of materials using the indentation techniques are limited to use in evaluating the fracture toughness of brittle materials. Furthermore, the conventional evaluation models using the indentation techniques are only effective when a subject brittle material is in a temperature range lower than the ductile-brittle transition temperature (DBTT) of the brittle material. If the brittle material is in a temperature range which is not lower than the ductile-brittle transition temperature (DBTT) of the brittle material, an indentation cannot form a crack in the brittle material, so that the fracture toughness evaluation of brittle materials using indentation techniques must be studied and developed.

DISCLOSURE OF INVENTION

Technical Problem

Accordingly, the present invention has been made keeping in mind the above problem occurring in the prior art, and an object of the present invention is to provide a method for evaluating the fracture toughness of a material using the continuous indentation technique, which executes a nondestructive evaluation of the fracture toughness of a brittle material using the continuous indentation technique.

Another object of the present invention is to provide a method for evaluating the fracture toughness of a material using the continuous indentation technique, which can evaluate the fracture toughness of the material using only the continuous indentation test data without requiring a test-piece to be cut from the material.

A further object of the present invention is to provide a method for evaluating the fracture toughness of a material using the continuous indentation technique, which can evaluate the fracture toughness of the material without limiting the size and shape of a test-piece or the material, and which easily and efficiently evaluates fracture toughness unlike a conventional evaluation method.

The present invention uses the idea of continuous damage mechanics (CDM) and critical void volume fraction (f) to determine the characteristic fracture initiation point (h*) of the indentation depth during or after the indentation process. The fracture toughness, which is evaluated using the continuous indentation test data according to the model of the present invention, is compared to the fracture toughness value determined by the standard fracture toughness evaluation technique.

Advantageous Effects

The present invention is advantageous in that it can precisely evaluate the fracture toughness of a brittle material using a nondestructive evaluation technique.

Unlike conventional fracture toughness evaluation methods which require test-pieces having specified crack growth directions and sizes to be cut from subject materials, the present invention can evaluate the properties and fracture toughness of a material using a nondestructive evaluation technique and an indentation tester placed on the material at a predetermined position without cutting the material, so that the present invention does not limit the size and shape of the material.

Furthermore, the present invention can be used to evaluate the fracture toughness of a material precisely using an indentation tester placed around a pipeline or an industrial structure before, during or after the practical operation thereof. In addition, the present invention can evaluate the fracture toughness of a material using a simple continuous indentation technique, thus increasing productivity and work efficiency while evaluating the fracture toughness.

BRIEF DESCRIPTION OF THE DRAWINGS

FIG. 1 is a sectional view illustrating the construction of a continuous indentation tester used in the present invention;

FIG. 2 is a graph illustrating a curve of indentation load-indentation depth of the present invention;

FIG. 3 is a view schematically illustrating the formation of voids in a material due to indentation;

FIG. 4 is a view schematically illustrating the progress of a ductile fracture according to an increase in the void volume fraction;

FIG. 5 is a graph illustrating effective elastic modulus ($E_{eff}$) as a function of indentation depth (h);

FIGS. 6 and 7 are graphs illustrating the shapes of curves of indentation load as a function of displacement during a fracture toughness test according to the fracture type;

FIGS. 8 and 9 are graphs illustrating effective elastic modulus as a function of indentation depth of a material during a fracture toughness test according to the fracture type;

FIG. 10 is a graph illustrating a method of determining a characteristic fracture initiation point of the indentation depth using the effective elastic modulus-indentation depth curve;

FIG. 11 is a graph illustrating a method of determining a characteristic fracture initiation point of the indentation depth using the effective elastic modulus-indentation depth curve and an extrapolation method; and FIG. 12 is a graph comparatively illustrating the fracture toughness values evaluated using the continuous indentation technique and CTOD.

BEST MODE FOR CARRYING OUT THE INVENTION

To solve the above-mentioned problems, an embodiment of the present invention provides a method of evaluating the fracture toughness of a material using a continuous indentation technique of continuously measuring an indentation load and an indentation depth while repeatedly applying and removing the load to and from the material, the method including the steps of: measuring a stress coefficient, a strain hardening modulus and a yield stress using the continuous indentation technique and calculating a reduced elastic modulus ($E_r$); calculating an effective elastic modulus ($E_{eff}$) from the reduced elastic modulus; determining an initial elastic modulus ($E_0$) from the elastic modulus in a first range of the effective elastic modulus, which was determined using a plurality of unloading curves obtained using the continuous indentation technique; setting a void volume fraction (f) to a specific value within a range from 0.13 to 0.17 when the fracture type of the material is a I-type fracture type, and setting the void volume fraction (f) to a specific value within a range from 0.23 to 0.27 when the fracture type of the material is a II-type fracture type; calculating a damage parameter (D) from the void volume fraction using the equation $$D = \frac{\pi}{\left(\frac{4}{3}\pi\right)^{\frac{2}{3}}} f^{\frac{2}{3}};$$

calculating a critical elastic modulus (E*) using the damage parameter; calculating a characteristic fracture initiation point (h*) of the indentation depth using the critical elastic modulus; and calculating the fracture toughness ($K_{JC}$) of the material using the characteristic fracture initiation point and the equation $$K_{JC} = \sqrt{2E_0\omega_f} = \sqrt{E_0 \lim_{h \to h^*} \int_0^h \frac{F}{A_C} dh} = \sqrt{\frac{E_0}{\pi} k' \ln\left(\frac{2R}{2R - h^*}\right)},$$

wherein k' represents the slope ($L_{max}/h_{max}$) between the maximum indentation load and the maximum indentation depth in the unloading curve.

In an effort to solve the above-mentioned problems, another embodiment of the present invention provides a method of evaluating the fracture toughness of a material using a continuous indentation technique of continuously measuring an indentation load and an indentation depth while repeatedly applying and removing the indentation load to and from the material, the method including the steps of: measuring a stress coefficient, a strain hardening modulus and a yield stress using the continuous indentation technique and calculating a reduced elastic modulus; calculating an effective elastic modulus from the reduced elastic modulus; determining an initial elastic modulus from an elastic modulus in a first range of the effective elastic modulus, which was determined using a plurality of unloading curves obtained using the continuous indentation technique; setting a void volume fraction to 0.20 when the fracture type of the material is not known; calculating a damage parameter from the void volume fraction using the equation $$D = \frac{\pi}{\left(\frac{4}{3}\pi\right)^{\frac{2}{3}}} f^{\frac{2}{3}};$$

calculating a critical elastic modulus ($E^*_{im}$) using the damage parameter; calculating a characteristic fracture initiation point ($h^*_{im}$) of the indentation depth using the critical elastic modulus; calculating the fracture toughness ($K_{JCim}$) of the material using the characteristic fracture initiation point of the indentation depth using the equation $$K_{JCim} = \sqrt{2E_0\omega_f} = \sqrt{E_0 \lim_{h \to h^*} \int_0^h \frac{F}{A_C} dh} = \sqrt{\frac{E_0}{\pi} k' \ln\left(\frac{2R}{2R - h^*_{im}}\right)};$$

and calculating a plastic zone size (PZS) using the fracture toughness, wherein k' represents the slope between the maximum indentation load and the maximum indentation depth in the unloading curve.

Critical indentation energy ($2\omega_f$) is calculated using the equation $$2\omega_f = \lim_{h \to h^*} \int_0^h \frac{F}{A_c} dh,$$

wherein $A_c$ represents a contact surface area between the material and an indenter, F represents the indentation load, h represents the indentation dept, and h* represents the characteristic fracture initiation point of the indentation depth.

The reduced elastic modulus is calculated using the equation $$E_r = \frac{\sqrt{\pi}}{2} S \frac{1}{\sqrt{A_c}},$$

wherein S represents the slope of the unloading curve.

The effective elastic modulus is calculated using the equation $$E_{eff} = \frac{1-v^2}{\left(\frac{1}{E_r} - \frac{1-v_i^2}{E_i}\right)} + \frac{1-v^2}{\left(\frac{2\sqrt{A_C}}{\sqrt{\pi}\,S} - \frac{1-v_i^2}{E_i}\right)},$$

wherein v and $v_i$ represent Poisson's ratios of the material and the indenter, respectively, and $E_i$ represents the elastic modulus of the indenter.

The critical elastic modulus is calculated using the equation $$E^* = E_0(1-D)$$

The characteristic fracture initiation point of the indentation depth is calculated using the equation $$h^* = \exp\left(\frac{\ln E^* - A}{B}\right).$$

The critical elastic modulus is calculated using the equation $$E^*_{im} = E_0(1-D)$$

The characteristic fracture initiation point of the indentation depth is calculated using the equation $$h^*_{im} = \exp\left(\frac{\ln E^*_{im} A}{B}\right).$$

The plastic zone size is calculated using the equation $$PZS = 2.5(K_{JCim}/YS)^2$$

, wherein, when the plastic zone size is not higher than 0.4, the void volume fraction is set to a specific value within a range from 0.13 to 0.17 and, when the plastic zone size is higher than 0.4, the void volume fraction is set to a specific value within a range from 0.23 to 0.27 and is used to calculate the fracture toughness of the material, and YS represents the yield stress of the material which is evaluated using the continuous indentation technique.

Mode for the Invention

Herein below, the present invention will be described in detail with reference to the accompanying drawings.

FIG. 1 is a sectional view showing the construction of a continuous indentation tester used in the present invention. To evaluate the properties of a material, the present invention uses an indentation tester 100 which is disclosed in Korean Patent Application No. 2001-16070 entitled "Indentation tester, method of providing indentation test data and evaluating the properties of a material using the indentation tester, and recording medium having the property evaluation method thereon".

The indentation tester 100 comprises a loading unit 110 to generate an indentation load using the rotation of a motor 111, a load sensor 123, and indenter holder 125, and an indenter 127.

The rotational force generated from the motor 111 rotates a ball screw 117 and rectilinearly moves an external ball screw nut 118 upwards and downwards in vertical directions. In the above case, vertical pressure is transmitted to a test-piece through the indenter 127, thus generating compressive stress. When the motor 111 is rotated and applies an indentation load to the test-piece, the load sensor 123 continuously measures the variation in the indentation load applied to the test-piece. Furthermore, a strain sensor provided in the continuous indentation tester 100 continuously measures the indentation depth of the indenter 127.

The indentation load and the indentation depth are measured to a predetermined depth using the load sensor 123 and the strain sensor and, thereafter, the indentation load and the indentation depth are measured again while rotating the motor 111 in a reverse direction and removing some of the indentation load from the indenter 127, thus continuously executing the process of determining the stress and modulus of strain at the same place. Thereafter, an indentation load is applied again to the indenter 127 through the above-mentioned method, thus further indenting the material surface and increasing the indentation depth and measuring the indentation load and indentation depth and, thereafter, the indentation load and the indentation depth are measured again while removing some of the indentation load from the indenter 127, thus continuously determining the stress and modulus of strain. Thus, by repeating the above-mentioned process, stress and strain modulus curves can be obtained at the same place.

The present invention uses a technique of evaluating the properties of a material using the continuous indentation tester 100 which can measure the properties of the material while repeatedly applying and removing indentation load to and from the material. The evaluation technique used in the present invention remains the same as that described in the related art and further explanation is thus not deemed necessary.

The fracture toughness ($K_{JC}$) on an infinite plane having a length 2a is calculated using Equation 1.

$$K_{JC} = \sigma_f \sqrt{\pi a} \qquad \text{[Equation 1]}$$

wherein $\sigma_f$ represents a remote tensile stress at the fracture. The remote tensile stress ($\sigma_f$) at the fracture is represented using Equation 2 according to Griffith's theory.

$$\sigma_f = \sqrt{\frac{2E\omega_f}{\pi a}} \qquad \text{[Equation 2]}$$

wherein E represents the elastic modulus, and $\omega_f$ represents energy absorbed by the material until the material is fractured. When Equation 1 and Equation 2 are combined together, the relationship between energy ($\omega_f$) and fracture toughness ($K_{JC}$) is represented using Equation 3.

$$K_{JC} = \sqrt{2E\omega_f} \qquad \text{[Equation 3]}$$

To evaluate the fracture toughness ($K_{JC}$) of the material using the continuous indentation technique, the energy ($\omega_f$) must be represented by indentation parameters. The stress triaxiality of the lower part of the indenter ranges between 2 and 3, and this restriction of the strain range of the lower part of the indenter is similar to that of the front part of a crack tip. Thus, if there is a characteristic fracture initiation point (h*) of the indentation depth during or after the indentation process, the indentation energy per unit contact surface area, which has been absorbed by the material to the indentation depth, is related to $\omega_f$.

FIG. 2 is a graph showing an indentation load-indentation depth curve. As shown in the graph, the critical indentation energy ($2\omega_f$) can be calculated using the indentation load-indentation depth curve.

$$2\omega_f = \lim_{h \to h^*} \int_0^h \frac{F}{A_c} dh \quad \text{[Equation 4]}$$

wherein F represents an indentation load, h represents an indentation depth, $A_C$ represents a contact surface area, and h* represents a characteristic fracture initiation point (the indentation depth corresponding to critical elastic modulus). $2\omega_f$ represents fracture energy, and the Arabic numeral 2 in front of $\omega_f$ is determined by the fact that two surfaces are formed in the upper and lower regions while a crack grows. In other words, $2\omega_f$ is primarily calculated using the data measured by the continuous indentation technique and the calculation results are, thereafter, used in Equation 3 along with the elastic modulus of the material, so that the fracture toughness of the material can be determined. To calculate $2\omega_f$ of Equation 4, the characteristic fracture initiation point (h*) of the indentation depth must be determined. To accomplish this object, the elastic modulus during the indentation process must be calculated as follows.

The reduced elastic modulus ($E_r$) can be calculated using Equation 5.

$$E_r = \frac{\sqrt{\pi}}{2} S \frac{1}{\sqrt{A_c}} \quad \text{[Equation 5]}$$

The effective elastic modulus can be analyzed from the reduced elastic modulus calculated using Equation 5.

When damage to the material placed under the indenter is increased and the indentation dept (h) is increased, the effective elastic modulus ($E_{eff}$) is reduced. Furthermore, the effective elastic modulus is represented by a mathematical function comprising the indentation parameters.

The effective elastic modulus can be analyzed from the reduced elastic modulus.

$$E_{eff} = \frac{1-v^2}{\left(\frac{1}{E_r} - \frac{1-v_i^2}{E_i}\right)} + \frac{1-v^2}{\left(\frac{2\sqrt{A_C}}{\sqrt{\pi} S} - \frac{1-v_i^2}{E_i}\right)} \quad \text{[Equation 6]}$$

wherein v and $v_i$ represent Poisson's ratios of the material and the indenter, respectively, $E_r$ represents reduced elastic modulus, $E_i$ represents the elastic modulus of the indenter, $A_c$ represents a contact surface area between the indenter and the material, and S represents the slope of the unloading curve. After indentation load is repeatedly applied to and removed from the material, the effective elastic modulus ($E_{eff}$) according to a variety of indentation depths is calculated from the unloading curves. Thereafter, the value of h* is calculated using the elastic modulus and the value of $2\omega_f$ is calculated prior to evaluating the fracture toughness ($K_{JC}$) as follows.

EXAMPLE 1

If the Type of Material is Known

In an indentation test, there is no prominent characteristics, such as crack growth, to indicate the fracture of a material, so that the characteristic fracture initiation point (h*) of the indentation depth cannot be measured through a direct method, but the point (h*) can be measured using an optical microscope or a scanning electron microscope. Thus, to determine the characteristic fracture initiation point (h*), the ideas of continuum damage mechanics (CDM) and the critical void volume fraction are adapted to the indentation process.

FIG. 3 is a view schematically showing the progress of a brittle fracture according to an increase in the void volume fracture (f) during a typical brittle fracture.

As shown in FIG. 3, when the indentation load is applied to the material, voids are formed in the material. Furthermore, the indentation load applied to the material increases, so that deformation occurs in the material, resulting in void growth and causing the voids to coalesce with neighboring voids and enlarging the void sizes. The mechanism relating to void generation, void growth and void coalescence during the brittle fracture is adapted to the present invention while considering the stress conditions in the indentation test.

FIG. 4 is a view schematically showing the formation of the voids in the material according to the indentation. As shown in the drawing, when an indentation load is applied to the material, the material is deformed to create an indentation depth (h). When the indentation depth increases, the deformation of the material at a position under the indenter increases, thus forming voids in the material. In other words, because the indentation load is compressive along a loading axis, the deformation region under the indenter is subjected to a compressive force. Thus, voids are formed in the material due to the partial shearing stress caused by the compressive force. When the indentation depth increases, the void volume fraction proportionally increases. This means that the material is damaged.

To measure the damage to the material, the damage parameter (D) defined using Equation 7 is used. The damage parameter (D) relates to the surface density of micro-defects in the material.

$$D = \frac{s_D}{s} \quad \text{[Equation 7]}$$

wherein s and $s_D$ are the overall sectional area of a loading region and a surface area occupied by the micro-defects on the overall sectional area, respectively. In Equation 7, the damage parameter (D) can be calculated from the variation in the elastic modulus using Lemaitre's strain equivalence principle.

$$D = 1 - \frac{E_{eff}}{E_0} \quad \text{[Equation 8]}$$

or $$E_{eff} = E_0(1-D)$$

wherein $E_{eff}$ represents the effective elastic modulus of the damaged material, and E represents the initial elastic modulus of the undamaged material.

Furthermore, the damage parameter is represented in relation to the void volume fraction as follows.

$$f = \frac{\frac{4}{3}\pi}{\pi^{\frac{3}{2}}} D^{\frac{3}{2}}$$ [Equation 9]

or $$D = \frac{\pi}{\left(\frac{4}{3}\pi\right)^{\frac{2}{3}}} f^{\frac{2}{3}}$$

To determine the critical elastic modulus from the relationship between the void volume fraction, the damage parameter and the elastic modulus, the critical void volume fraction principle is used. The experiments of Brown and Embury and the experiments of Goods and Brown show that the voids start to coalesce together when the void volume fraction (f) ranges from about 0.13 to 0.17, and the void coalescence starts when the void volume fraction (f) is not higher than 0.2. Furthermore, the numerical analysis of Anderson shows that the stable crack growth of a brittle material starts when the void volume fraction (f) ranges from about 0.23 to 0.27. Tebogard used the above-mentioned standard to the cup-corn fracture analysis.

According to the experiments and analyses, the void volume fraction ($f_C$), at which the void coalescence starts, ranges from 0.13 to 0.17, while the void volume fraction ($f_F$), at which the stable crack growth starts, ranges from 0.23 to 0.27. The two void volume fractions ($f_C$ and $f_F$) are used to determine the critical elastic modulus. If the fracture type of a material is known, the damage parameter (D) of the material can be calculated as follows. If the material is a Type-I material, the damage parameter (D) of the material can be determined using a specified value within a range from 0.13 to 0.17, corresponding to the properties of the material, as the void volume fraction in Equation 9. If the material is a Type-II material, the damage parameter (D) can be determined using a specified value within a range from 0.23 to 0.27 as the void volume fraction in Equation 9.

TABLE 1

| Type | Material | Exact value KJC (MPa m^0.5) | 0.13 | 0.15 | 0.17 | 0.23 | 0.25 | 0.27 |
|---|---|---|---|---|---|---|---|---|
| Type I | SA508 | 144 | 117 | 131 | 145 | | | |
| | SUJ2 | 111 | 99 | 108 | 117 | | | |
| | SKS3 | 95 | 111 | 128 | 151 | | | |
| | S45C | 150 | 115 | 131 | 153 | | | |
| Type II | X70 | 380 | | | | 280 | 327 | 385 |
| | X65 | 300 | | | | 246 | 301 | 384 |
| | SCM21 | 261 | | | | 184 | 210 | 244 |
| | SUS303 | 251 | | | | 199 | 241 | 296 |

Table 1 shows variation in the evaluated fracture toughness of a material according to variation in the void volume fraction of the material. As illustrated in Table 1, every material has a specific void volume fraction which can be used to evaluate the fracture toughness of the material most precisely (as underlined and bold in the Table). Therefore, it is preferable to evaluate the fracture toughness of the materials after setting the appropriate void volume fractions according to the properties and types of the materials.

The Type-I materials and the Type-II materials will be described in detail in the description of the experimental results. The damage parameter (D), which was determined for a Type-I material using the void volume fraction (f) within the range from 0.13 to 0.17, is defined as $D_C$, while the damage parameter (D), which was determined for a Type-II material using the void volume fraction (f) within the range from 0.23 to 0.27, is defined as $D_F$. However, if the fracture type of a material is not known, the damage parameter of the material can be determined through iteration, as will be described in Example 2.

The determined damage parameters are used to calculate the critical elastic moduli (E*) of the materials.

$E^* = E_0(1-D_C)$ for Type-I or $E^* = E_0(1-D_F)$ for Type-II [Equation 10]

In this case, the value E is the elastic modulus obtained from the analysis of the first unloading curve of a plurality of unloading curves determined through repeated loading and unloading. In other words, the value E is the initial elastic modulus of an undamaged material as described above. Damage to the material caused by voids at the initial stage of indentation is negligible, so that the state of the material at the initial stage of indentation may be considered an undamaged state.

Thereafter, the characteristic fracture initiation point (h*) of the indentation depth can be calculated from the critical elastic modulus.

$$h^* = \exp\left(\frac{\ln E^* - A}{B}\right)$$ [Equation 11]

FIG. 5 is a graph showing the relationship between the effective elastic modulus ($E_{eff}$) and the indentation depth (h). The relationship between the effective elastic modulus and the indentation depth may be defined as illustrated in the graph of the drawing. If the critical elastic modulus (E*) was determined, the indentation depth corresponding to the critical elastic modulus (E*) can be determined from the characteristic fracture initiation point (h*) of the indentation depth. In this case, the characteristic fracture initiation point must be placed between the points in the graph of FIG. 5 or must be determined using an extrapolation method, so that the Y-axial component of a line obtained through an ln-ln fitting of curves of the critical elastic modulus and the characteristic fracture initiation point of the indentation depth is defined as A, and the slope of the line obtained through the fitting is defined as B. The characteristic fracture initiation point (h*) of the indentation depth can be determined using Equation 11, the values A and B and the critical elastic modulus (E*) having been obtained using Equation 10.

Thereafter, the fracture toughness of the material can be evaluated using the characteristic fracture initiation point and Equation 12.

$$K_{JC} = \sqrt{\frac{E_0}{\pi} k' \ln\left(\frac{2R}{2R - h^*}\right)}$$ [Equation 12]

wherein k' represents the slope ($L_{max}/h_{max}$) of a loading curve, and R is the radius of the indenter. Equation 12 is the equation which is created using only the data obtained from combination of Equations 3 and 4 during an indentation process. In Equation 12, the value $E_0$ can be determined from the first unloading curve, while the value h* can be determined from the relationship between the critical void volume fraction, the damage parameter and the critical elastic modulus (E*).

Thus, the present invention can evaluate the fracture toughness of a material using the continuous indentation technique including the above-mentioned continuous processes.

EXAMPLE 2

If the Type of Material is Not Known

In Example 1, the method of evaluating the fracture toughness of a material, whose fracture type is known, has been described.

However, in the case of a material whose fracture type is not known, it is impossible to previously determine the critical void volume fraction of the material, so that neither the critical elastic modulus nor the characteristic fracture initiation point of the indentation depth may be determined.

In the above case, the damage parameter ($D_{0.20}$) and the critical elastic modulus of the material may be determined using the void volume fraction set to 0.20, which is the average of the void volume fractions of the Type-I materials and the Type-II materials.

Described in detail, the damage parameter ($D_{0.20}$) is determined by substitution of 0.20 for the void volume fraction (f) in Equation 9 and the critical elastic modulus is calculated. The critical elastic modulus in the above case is represented by $E^*_{im}$.

$$E^*_{im} = E_0(1 - D_{0.20}) \quad \text{[Equation 13]}$$

The fracture toughness of the material is calculated by substitution of the critical elastic modulus ($E^*_{im}$) in Equation created by transforming Equation 11 and Equation 12.

$$h^*_{im} = \exp\left(\frac{\ln E^*_{im} - A}{B}\right) \quad \text{[Equation 14]}$$

$$K_{JCim} = \sqrt{\frac{E_0}{\pi} k' \ln\left(\frac{2R}{2R - h^*_{im}}\right)} \quad \text{[Equation 15]}$$

The plastic zone size (PZS) is calculated from the determined fracture toughness of the material.

$$PZS = 2.5(K_{JCim}/YS)^2 \quad \text{[Equation 16]}$$

wherein YS represents the yield stress of the material determined using the continuous indentation technique.

When the plastic zone size determined using Equation 16 is not larger than 0.4(m), the material is determined to be Type-I material having a void volume fraction ranging from 0.13 to 0.17. However, when the plastic zone size is larger than 0.4 (m), the material is determined to be Type-II material having a void volume fraction ranging from 0.23 to 0.27. Thereafter, the fracture toughness of the material is evaluated using the method described in Example 1. Described in detail, in the method of Example 2, the plastic zone size is determined using a void volume fraction set to 0.20, which is the average of the void volume fraction of the Type-I materials and the void volume fraction of the Type-II materials. Thereafter, the void volume fraction is more precisely determined using the plastic zone size prior to determining the fracture toughness of the material.

EXPERIMENTAL RESULTS

The values of critical Crack Tip Opening Displacement (CTOD) are classified into $\delta_C$, $\delta_U$ and $\delta_m$, in which the CTOD values of brittle materials are typically represented by $\delta_U$ and $\delta_m$. While $\delta_m$ is the CTOD value when the maximum load plane is obtained, $\delta_U$ is the CTOD value when an unstable crack growth starts. The relationship between the above-mentioned CTOD values is illustrated in FIG. 6 and FIG. 7. FIG. 6 and FIG. 7 are graphs illustrating the shapes of curves of indentation load as a function of displacement at a crack tip during a fracture toughness test according to the fracture type. FIG. 6 shows the curve of a $\delta_U$-type material, while FIG. 7 shows the curve of a $\delta_m$-type material. In the present invention, the materials showing a $\delta_U$-type fracture behavior characteristic of relatively brittle materials are classified as Type-I materials, while the materials showing a $\delta_m$-type fracture behavior characteristic of relatively soft materials are classified as Type-II materials.

The $\delta_U$-type materials are the relatively brittle materials and have a smaller resistance to the force that deforms the ligament between voids in comparison to the $\delta_m$-type materials, so that the load support power of the $\delta_U$-type materials is quickly reduced just after the void coalescence starts. However, in the $\delta_m$-type materials, the stable crack growth starts and the load support power is gradually reduced, so that the $\delta_m$-type materials maintain desired load support power after the void coalescence starts. Thus, the value $f_C$ may be used as the critical void volume fraction of the $\delta_U$-type material (type-I material), while the value $f_F$ may be used as the critical void volume fraction of the $\delta_M$-type material (type-II material). The values $f_C$ and $f_F$ may be changed to corresponding damage parameters $D_C$ and $D_F$ using Equation 8. Furthermore, the elastic moduli E* ($E_C$ and $E_F$) corresponding to the damage parameters may be determined using Equation 6. Thus, the value h* is determined from the value h corresponding to the critical elastic modulus, in which the relationship $E^* = E_C$ is used in the type-I materials, while the relationship $E^* = E_F$ is used in the type-II materials.

FIGS. 8 and 9 are graphs illustrating the relationship between the effective elastic modulus and the indentation depth according to the fracture type, in which FIG. 8 shows the relationship of the Type-I material, and FIG. 9 shows the relationship of the Type-II material. FIG. 10 is a graph showing a method of determining the characteristic fracture initiation point of the indentation depth using the effective elastic modulus-indentation depth curve. FIG. 11 is a graph showing a method of determining the characteristic fracture initiation point of the indentation depth using the effective elastic modulus-indentation depth curve and an extrapolation method. FIG. 10 is a graph of a Type-I material having the relationship $E^* = E_C$, FIG. 11 is a graph of a Type-II material having the relationship $E^* = E_F$.

FIG. 12 is a graph comparatively illustrating the fracture toughness values evaluated using the continuous indentation technique and CTOD.

As shown in FIG. 12, the fracture toughness of thirteen materials, evaluated using the continuous indentation technique which is the nondestructive evaluation technique according to the present invention, is almost equal to the fracture toughness evaluated using the conventional CTOD technique. Thus, the method of evaluating the fracture toughness of a material using the nondestructive evaluation technique according to the present invention can be used as an effective technique substituting for the conventional destructive evaluation technique.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of evaluating the fracture toughness of a material using a continuous indentation technique, said continuous indentation technique continuously measuring an indentation load and an indentation depth while a continuous indentation test with an indenter repeatedly applies the indentation load to and removes the indentation load from the material and then evaluates properties of the material using a relationship between the indentation load and the indentation depth, the method comprising the steps of:

measuring a stress coefficient, a strain hardening modulus and a yield stress using the continuous indentation technique and calculating a reduced elastic modulus ($E_r$) of the material;

calculating an effective elastic modulus ($E_{eff}$) from the reduced elastic modulus;

determining an initial elastic modulus ($E_0$) from an elastic modulus in a first range of the effective elastic modulus, which was determined using a plurality of unloading curves obtained using the continuous indentation technique;

setting a void volume fraction (f) to a specific value within a range from 0.13 to 0.17 when a fracture type of the material is a I-type fracture type, and setting the void volume fraction (f) to a specific value within a range from 0.23 to 0.27 when the fracture type of the material is a II-type fracture type;

calculating a damage parameter (D) from the void volume fraction using an equation $$D = \frac{\pi}{\left(\frac{4}{3}\pi\right)^{\frac{2}{3}}} f^{\frac{2}{3}};$$

calculating a critical elastic modulus ($E^*$) using the damage parameter;

calculating a characteristic fracture initiation point ($h^*$) of the indentation depth using the critical elastic modulus;

and calculating the fracture toughness ($K_{JC}$) of the material using the characteristic fracture initiation point of the indentation depth using an equation $$K_{JC} = \sqrt{2E_0 \omega_f} = \sqrt{E_0 \lim_{h \to h^*} \int_0^h \frac{F}{A_C} dh} = \sqrt{\frac{E_0}{\pi} k' \ln\left(\frac{2R}{2R - h^*}\right)},$$

wherein $2\omega_f$ is a critical indentation energy, $A_C$ is a contact surface area between the material and the indenter, F is the indentation load, R is a radius of the indenter of the continuous indentation tester, and k' represents a slope ($L_{max}/h_{max}$) between a maximum indentation load and a maximum indentation depth in an unloading curve.

2. A method of evaluating the fracture toughness of a material using a continuous indentation technique, said continuous indentation technique continuously measuring an indentation load and an indentation depth while a continuous indentation test with an indenter repeatedly applies the indentation load to and removes the indentation load from the material and then evaluates properties of the material using a relationship between the indentation load and the indentation depth, the method comprising the steps of:

measuring a stress coefficient, a strain hardening modulus and a yield stress using the continuous indentation technique and calculating a reduced elastic modulus of the material;

calculating an effective elastic modulus from the reduced elastic modulus;

determining an initial elastic modulus ($E_0$) from an elastic modulus in a first range of the effective elastic modulus, which was determined using a plurality of unloading curves obtained using the continuous indentation technique;

setting a void volume fraction (f) to 0.20 when a fracture type of the material is not known;

calculating a damage parameter (D) from the void volume fraction using an equation $$D = \frac{\pi}{\left(\frac{4}{3}\pi\right)^{\frac{2}{3}}} f^{\frac{2}{3}};$$

calculating a critical elastic modulus ($E^*_{im}$) using the damage parameter;

calculating a characteristic fracture initiation point ($h^*_{im}$) of the indentation depth using the critical elastic modulus;

calculating the fracture toughness ($K_{JCim}$) of the material using the characteristic fracture initiation point of the indentation depth using an equation $$K_{JCim} = \sqrt{2E_0 \omega_f} = \sqrt{E_0 \lim_{h \to h^*} \int_0^h \frac{F}{A_C} dh}$$
$$= \sqrt{\frac{E_0}{\pi} k' \ln\left(\frac{2R}{2R - h^*_{im}}\right)};$$

and calculating a plastic zone size (PZS) using the fracture toughness, wherein $2\omega_f$ is a critical indentation energy, $A_C$ is a contact surface area between the material and the indenter, F is the indentation load, R is a radius of the indenter of the continuous indentation tester, and k' represents a slope between a maximum indentation load and a maximum indentation depth in an unloading curve.

3. The method of evaluating the fracture toughness of the material using the continuous indentation technique according to claim 1 or 2, wherein critical indentation energy ($2\omega_f$) is calculated using an equation $$2\omega_f = \lim_{h \to h^*} \int_0^h \frac{F}{A_c} dh,$$

wherein $A_c$ is a contact surface area between the material and an indenter, F is the indentation load, h is the indentation depth, and $h^*$ is the characteristic fracture initiation point of the indentation depth.

4. The method of evaluating the fracture toughness of the material using the continuous indentation technique according to claim 1 or 2, wherein the reduced elastic modulus ($E_r$) is calculated using an equation $$E_r = \frac{\sqrt{\pi}}{2} S \frac{1}{\sqrt{A_c}},$$

wherein S is a slope of the unloading curve.

5. The method of evaluating the fracture toughness of the material using the continuous indentation technique according to claim 1 or 2,
wherein the effective elastic modulus is calculated using an equation $$E_{\text{eff}} = \frac{1-v^2}{\left(\frac{1}{E_r} - \frac{1-v_i^2}{E_i}\right)} + \frac{1-v^2}{\left(\frac{2\sqrt{A_C}}{\sqrt{\pi} S} - \frac{1-v_i^2}{E_i}\right)},$$

wherein v and $v_i$ are Poisson's ratios of the material and the indenter, respectively, S is a slope of the unloading curve and $E_i$ is an elastic modulus of the indenter.

6. The method of evaluating the fracture toughness of the material using the continuous indentation technique according to claim 1,
wherein the critical elastic modulus is calculated using an equation $$E^* = E_0(1-D).$$

7. The method of evaluating the fracture toughness of the material using the continuous indentation technique according to claim 1,
wherein the characteristic fracture initiation point of the indentation depth is calculated using an equation $$h^* = \exp\left(\frac{\ln E^* - A}{B}\right),$$

wherein A is a Y-axial component of a line obtained through an ln-ln fitting of curves of the critical elastic modulus ($E^*$) and the characteristic fracture initiation point ($h^*$) of the indentation depth, and B represents a slope of the line obtained through the fitting.

8. The method of evaluating the fracture toughness of the material using the continuous indentation technique according to claim 2,
wherein the critical elastic modulus is calculated using an equation $$E^*_{im} = E_0(1-D).$$

9. The method of evaluating the fracture toughness of the material using the continuous indentation technique according to claim 2,
wherein the characteristic fracture initiation point of the indentation depth is calculated using an equation $$h^*_{im} = \exp\left(\frac{\ln E^*_{im-} A}{B}\right),$$

wherein A is a Y-axial component of a line obtained through an ln-ln fitting of curves of the critical elastic modulus ($E^*_{im}$) and the characteristic fracture initiation point ($h^*_{im}$) of the indentation depth, and B represents a slope of the line obtained through the fitting.

10. The method of evaluating the fracture toughness of the material using the continuous indentation technique according to claim 2,
wherein the plastic zone size is calculated using an equation $$PZS = 2.5(K_{JCim}/YS)^2,$$

wherein, when the plastic zone size is less than or equal to 0.4, the void volume fraction is set to a specific value within a range from 0.13 to 0.17, and when the plastic zone size is more than 0.4, the void volume fraction is set to a specific value within a range from 0.23 to 0.27 and is used to calculate the fracture toughness of the material, and YS represents the yield stress of the material which is evaluated using the continuous indentation technique.

* * * * *